(12) United States Patent
Ueda

(10) Patent No.: US 10,049,180 B2
(45) Date of Patent: Aug. 14, 2018

(54) ELECTRONIC MEDICAL RECORD APPARATUS AND RECORDING MEDIUM

(71) Applicant: KONICA MINOLTA, INC., Chiyoda-ku, Tokyo (JP)

(72) Inventor: Yutaka Ueda, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 252 days.

(21) Appl. No.: 14/080,754

(22) Filed: Nov. 14, 2013

(65) Prior Publication Data
US 2014/0172458 A1    Jun. 19, 2014

(30) Foreign Application Priority Data
Dec. 14, 2012  (JP) ................... 2012-273426

(51) Int. Cl.
G16H 30/00  (2018.01)
G06F 19/00  (2018.01)
G16H 30/20  (2018.01)

(52) U.S. Cl.
CPC ........... *G06F 19/321* (2013.01); *G16H 30/00* (2018.01); *G16H 30/20* (2018.01)

(58) Field of Classification Search
CPC ...... G06F 19/321; G06Q 50/24; G16H 30/00; G16H 30/20; G16H 30/40
See application file for complete search history.

(56) References Cited

U.S. PATENT DOCUMENTS

2001/0052933 A1* 12/2001 Nybo ............... G06F 17/30265
348/207.99
2006/0116904 A1*  6/2006 Brem .................... G06F 19/322
705/2

(Continued)

FOREIGN PATENT DOCUMENTS

JP    2002215797 A    8/2002
JP    2009022566 A    2/2009

(Continued)

OTHER PUBLICATIONS

Japanese Office Action (and English translation thereof) dated Mar. 8, 2016, issued in counterpart Japanese Application No. 2012-273426.

*Primary Examiner* — Minnah L Seoh
(74) *Attorney, Agent, or Firm* — Holtz, Holtz & Volek PC

(57) ABSTRACT

An electronic medical record apparatus is connected to an image generation apparatus which performs photographing to generate a medical image. The electronic medical record apparatus includes: a storage member; a patient specifying member to receive an input of specifying a patient to be examined; a display member to display a medical record screen for displaying electronic medical record information pertaining to the specified patient; a fetch instruction member, provided on the medical record screen, to receive an instruction to fetch the generated medical image; a control member to cause the storage member to store the medical image transmitted from the image generation apparatus so that the medical image is correlated with patient information of the patient whose medical record screen is currently displayed in the display member, when the fetch instruction member receives the instruction to fetch the medical image.

5 Claims, 7 Drawing Sheets

(56) References Cited

U.S. PATENT DOCUMENTS

2006/0261296 A1* 11/2006 Heath .................. A61B 6/4494
250/580
2010/0049548 A1    2/2010 Kubota

FOREIGN PATENT DOCUMENTS

| JP | 2009211647 A  | 9/2009 |
| JP | 2010-124943 A | 6/2010 |
| JP | 2010125021 A  | 6/2010 |
| WO | 2008090676 A1 | 7/2008 |

* cited by examiner

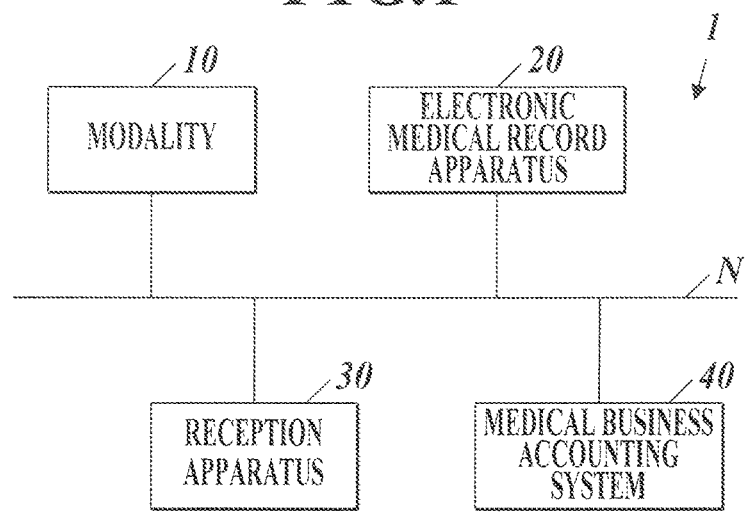
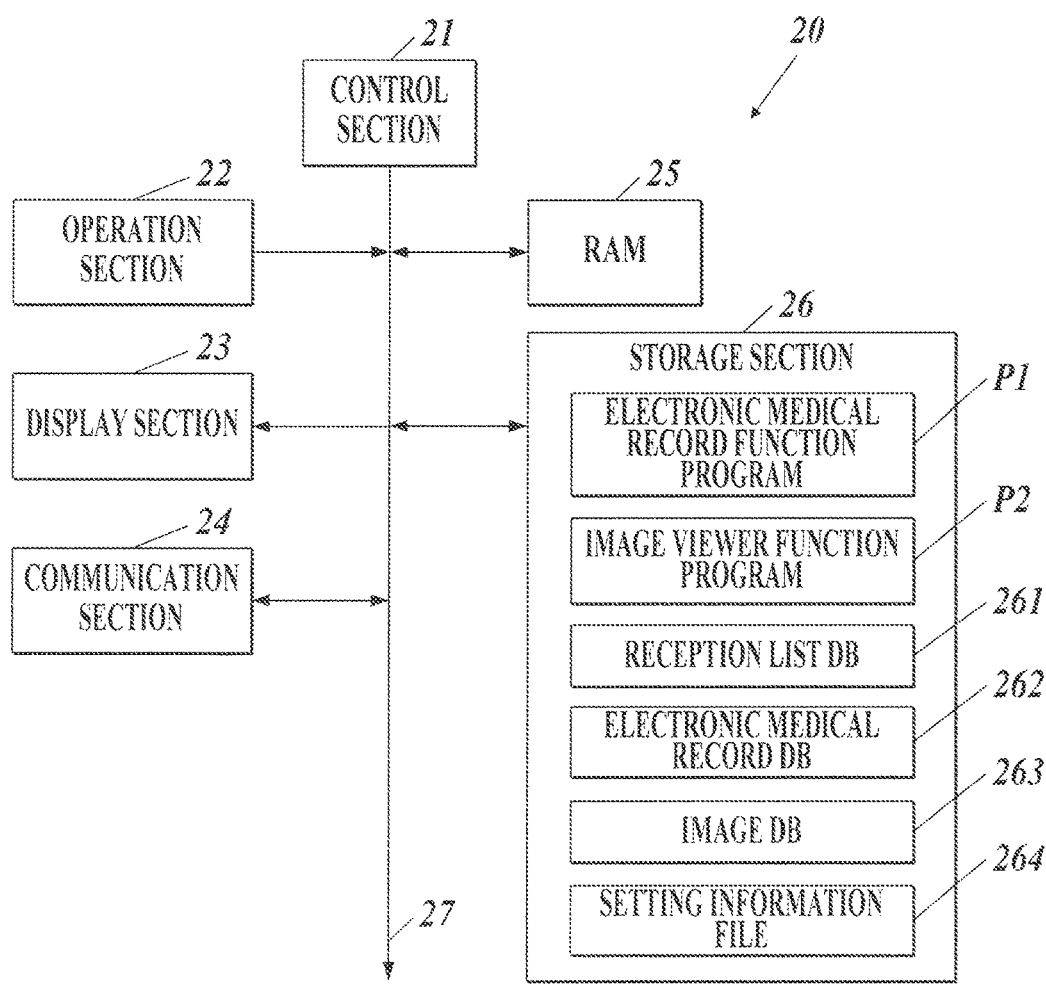

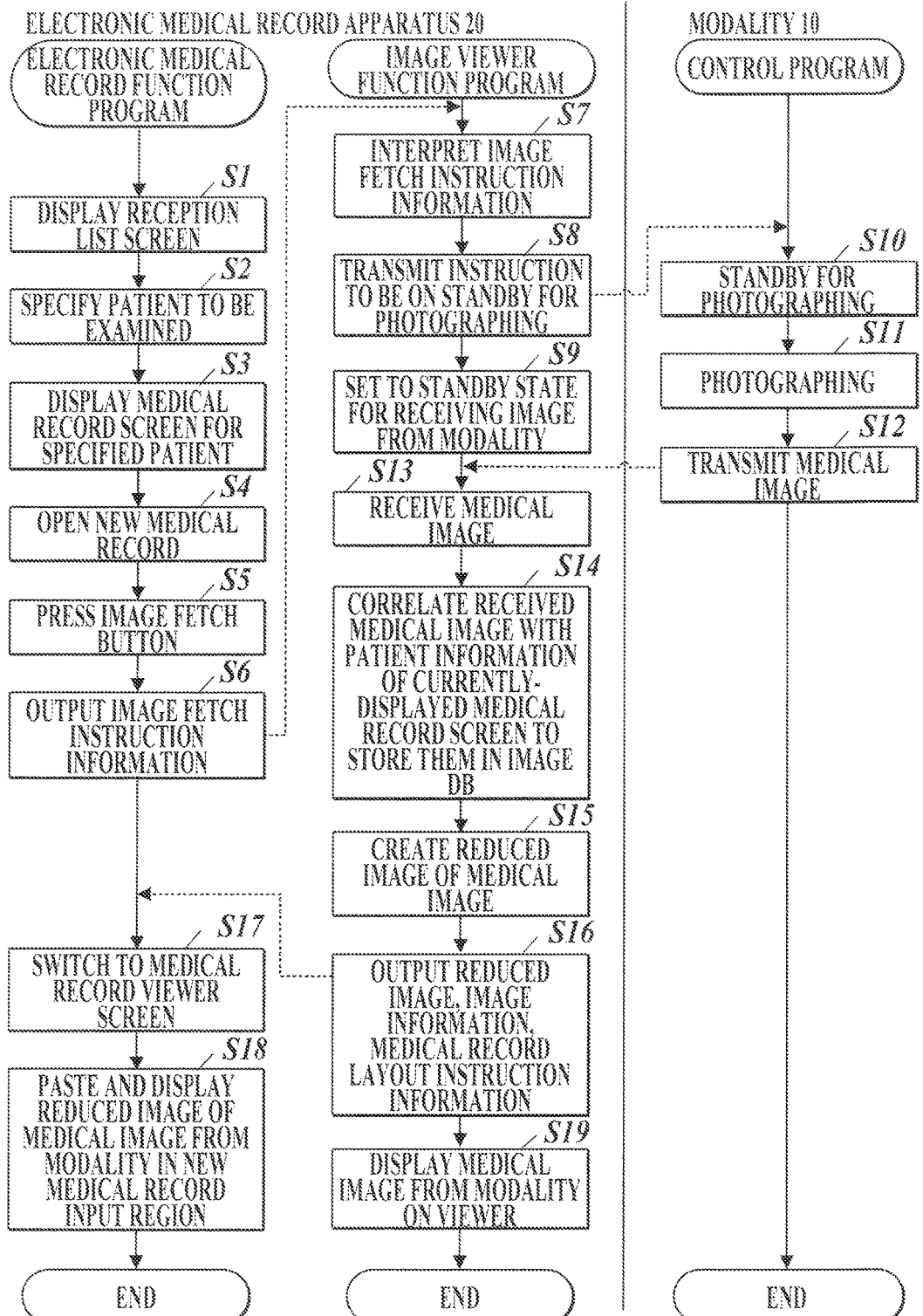

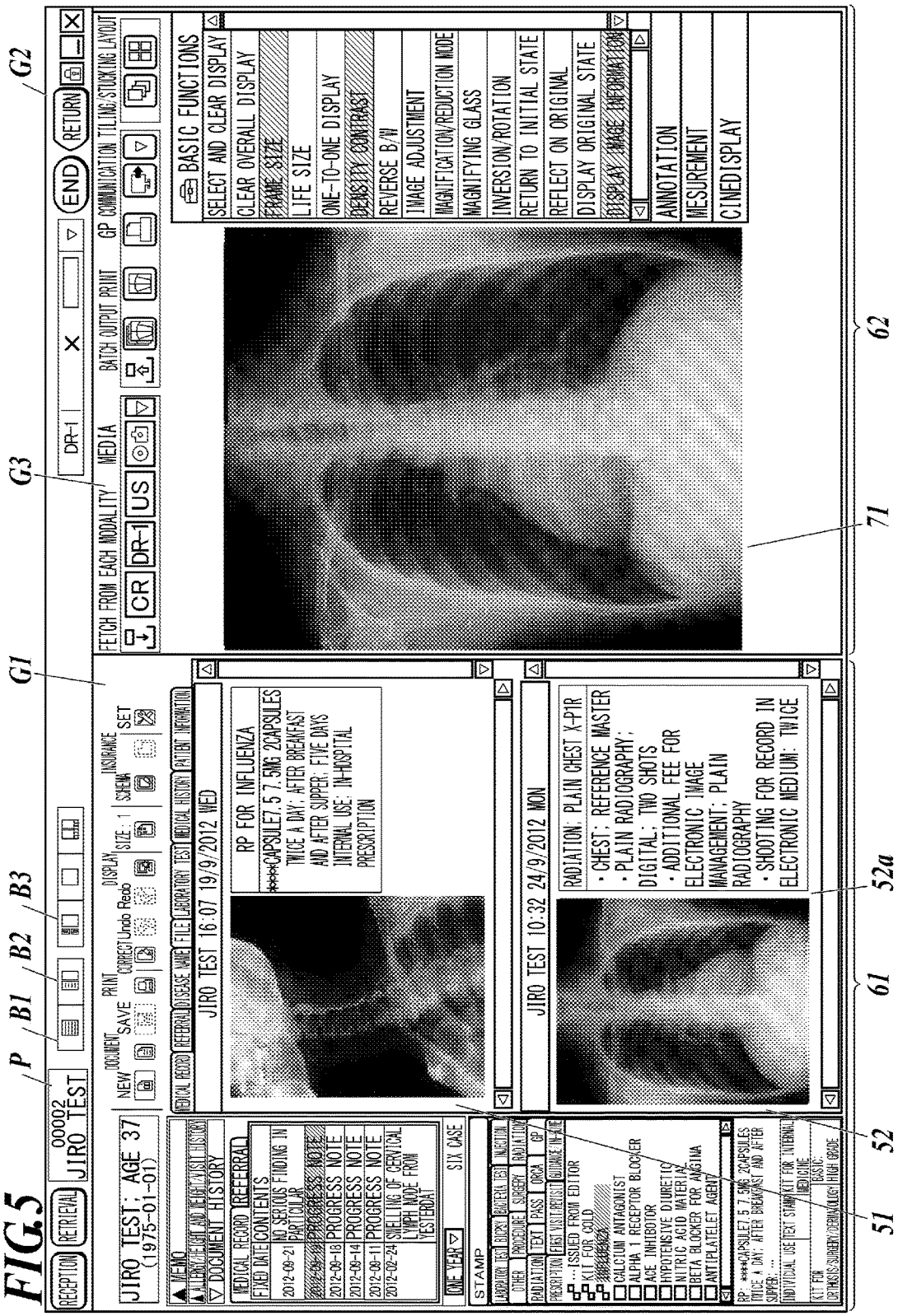

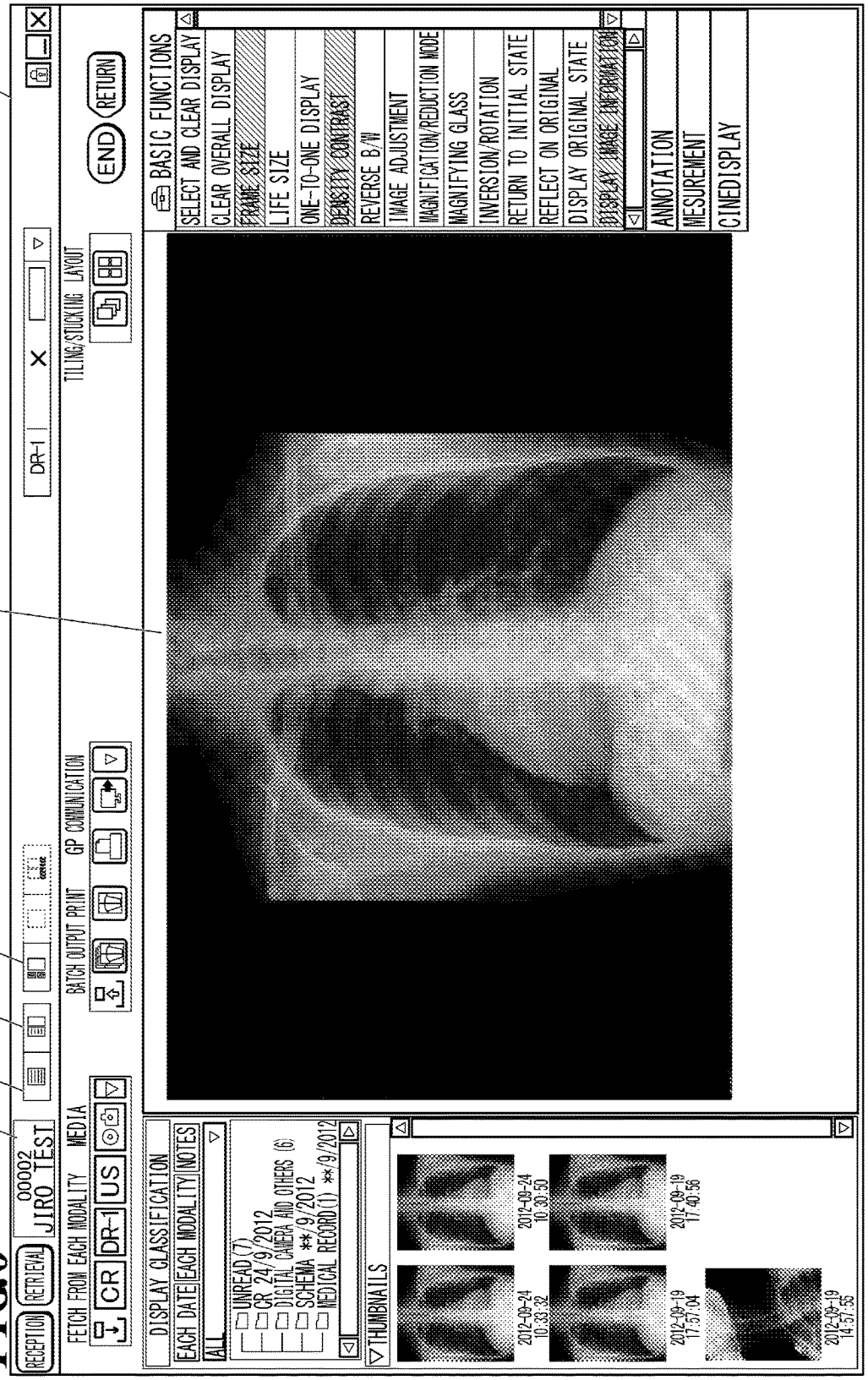

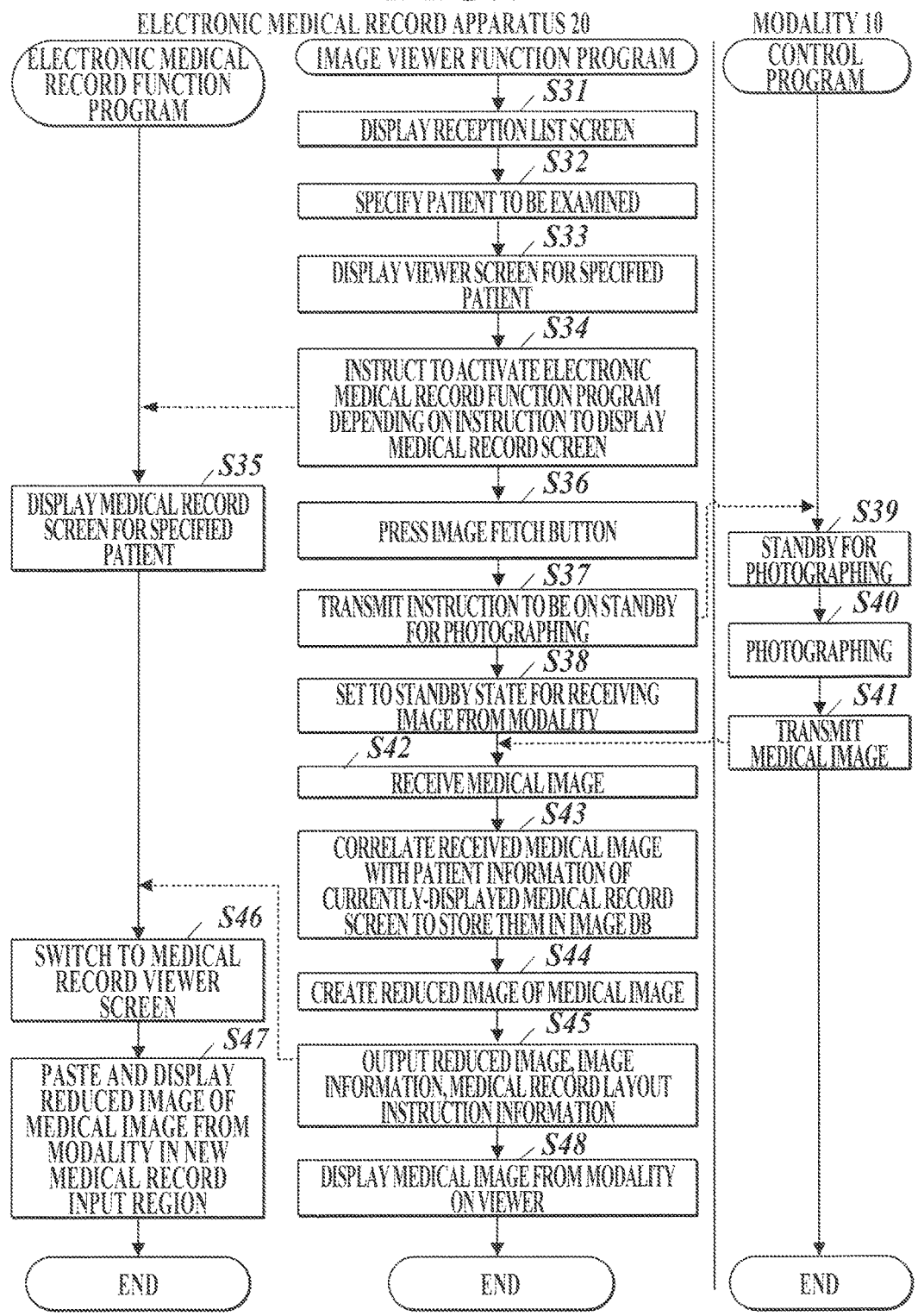

ELECTRONIC MEDICAL RECORD APPARATUS AND RECORDING MEDIUM

BACKGROUND OF THE INVENTION

Field of the Invention

The present invention relates to an electronic medical record apparatus and a recording medium.

Description of Related Art

Heretofore, there has been known a medical image management apparatus (PACS: Picture Archiving and Communication System) which stores in a database medical images taken by various modalities such as Computed Radiography (CR) and Flat Panel Display (FPD) apparatuses so that the medical images are correlated respectively with pieces of patient information, manages them, and displays the medical images on a viewer screen so as to provide the same to a doctor for radiologic interpretation and diagnosis.

Generally, photographing order information needs to be issued for photographing using modalities. In the modalities, photographing is performed according to the photographing order information, and obtained medical images are correlated with pieces of patient information of the photographing order information. However, in a small-scale medical facility such as an office of a practitioner and a clinic, in many cases, there is only one (1) doctor who performs diagnosis of patients, and the number of installed modalities is small. In this case, taking the time to issue the photographing order information complicates the procedure.

Therefore, there has been disclosed a medical image management apparatus which includes an image fetch button on a viewer screen, and when the viewer screen of a patient to be examined is opened and the image fetch button thereon is pressed, stores the medical images transmitted from the modalities so that the medical images are correlated respectively with pieces of patient information of the patient concerned, and displays the medical images on the viewer screen (for example, see Japanese Patent Application Laid-open No. 2010-124943).

Meanwhile, in medical facilities, the use of an electronic medical record apparatus, as well as the use of the above-described medical image management apparatus for performing radiologic interpretation and diagnosis, has been increased. The electronic medical record apparatus makes information electronically available, which information has been written in a paper medical record and is relevant to disease conditions of patients and/or prescription therefor, and stores and manages the information. The electronic medical record apparatus performs: record of electronic medical record information; transmission of treatment/prescription contents to a medical business accounting system (Receipt Computer); and so on. Some conventional electronic medical record apparatuses can issue the photographing order information.

However, in the case that the electronic medical record apparatus issues the photographing order information, separate operations including displaying a list of pieces of photographing order information in a console of a modality in a photographing room, selecting the photographing order information of a photographing object, and confirming an image display, become necessary. Such operations are very complicated and inefficient for being managed by one (1) doctor. Additionally, in order to paste the medical images obtained by photographing in the electronic medical record information, operations to obtain the medical images from the modalities and/or the medical image management apparatus and to paste the medical images in the information become necessary, and such operations are troublesome.

SUMMARY OF THE INVENTION

An object of the present invention is to enable an electronic medical record apparatus to easily correlate each medical image, which has been taken by modalities, with each piece of patient information, so that operability and efficiency of the electronic medical record apparatus at the time of diagnosis are improved.

In order to achieve at least one of the above-described objects, an electronic medical record apparatus, in which a first aspect of the present invention is reflected, is connected to an image generation apparatus which performs photographing of a diagnosis target region of a patient to generate a medical image, and includes: a storage member; a patient specifying member to receive an input of specifying a patient to be examined; a display member to display a medical record screen in which electronic medical record information pertaining to the patient specified by the patient specifying member is displayed; a fetch instruction member, provided on the medical record screen displayed in the display member, to receive an instruction to fetch the medical image which is generated in the image generation apparatus; and a control member to cause the storage member to store the medical image which has been transmitted from the image generation apparatus so that the medical image is correlated with patient information of the patient whose medical record screen is currently displayed in the display member, when the fetch instruction member receives the instruction to fetch the medical image.

Preferably, in the above the electronic medical record apparatus, the medical record screen includes a new medical record input region in which new electronic medical record information is input, and the control member pastes the medical image, which has been transmitted from the image generation apparatus, in the new medical record input region on the medical record screen displayed in the display member, when the fetch instruction member receives the instruction to fetch the medical image.

Preferably, the above the electronic medical record apparatus further includes a setting member to receive an input of setting as to whether or not to paste the medical image transmitted from the image generation apparatus in the new medical record input region.

Preferably, in the above the electronic medical record apparatus, the medical image to be pasted in the new medical record input region is a reduced image obtained by reducing the medical image.

A computer readable recording medium, in which a second aspect of the present invention is reflected, records a program causing a computer to function as described below, the computer being used in an electronic medical record apparatus connected to an image generation apparatus so that data transmission/reception can be performed between the apparatuses. The image generation apparatus performs photographing of a diagnosis target region of a patient to generate a medical image. The computer functions as: a patient specifying member to receive an input of specifying patient information of a patient to be examined; a display member to display a medical record screen in which electronic medical record information pertaining to the patient specified by the patient specifying member is displayed; a fetch instruction member, provided on the medical record screen displayed in the display member, to receive an instruction to fetch the medical image which is generated in the image generation apparatus; and a control member to cause the storage member to store the medical image which has been transmitted from the image generation apparatus so that the medical image is correlated with the patient information of the patient whose medical record screen is currently displayed in the display member, when the fetch instruction member receives the instruction to fetch the medical image.

BRIEF DESCRIPTION OF THE DRAWINGS

The present invention will become more fully understood from the detailed description given hereinbelow and the appended drawings, and thus are not intended as a definition of the limits of the present invention, and wherein:

FIG. 1 is a system configuration diagram of a diagnosis system;

FIG. 2 is a block diagram illustrating a functional configuration of an electronic medical record apparatus;

FIG. 3 is a diagram illustrating a flow of image fetch/display processing which is executed by the electronic medical record apparatus and a modality;

FIG. 4A is a diagram illustrating an example of a medical record screen;

FIG. 4B is a diagram illustrating an example of a medical record screen in which new medical record input region is displayed;

FIG. 5 is a diagram illustrating an example of a medical record viewer screen;

FIG. 6 is a diagram illustrating an example of a viewer screen; and

FIG. 7 is a diagram illustrating a variation of the image fetch/display processing.

PREFERRED EMBODIMENT OF THE PRESENT INVENTION

Hereinafter, a preferred embodiment of the present invention will be described in detail with reference to the attached drawings. In this regard, however, the scope of the present invention is not limited to illustrated examples.

First, a configuration according to this embodiment will be described.

[Configuration of Diagnosis System]

FIG. 1 illustrates an example of an overall configuration of a diagnosis system 1 according to the embodiment.

The diagnosis system 1 is a system to be applied to a relatively small-scale medical facility such as an office of a practitioner and a clinic, and as illustrated in FIG. 1, is configured to include a modality 10, an electronic medical record apparatus 20, a reception apparatus 30, and a medical business accounting system 40. The respective apparatuses/systems constituting the diagnosis apparatus 1 are connected to one another so as to enable data communication among them via a communication network N such as a LAN (Local Area Network).

The modality 10 is an image generation apparatus which is installed in a photographing room and performs photographing of each diagnosis target region of each patient to generate a digital medical image. As the modality 10, there can be adopted an X-ray image photographing apparatus such as a CR apparatus and FPD apparatus, an ultrasound diagnosis apparatus (US), and so on.

The electronic medical record apparatus 20 is a computer apparatus which is installed in an examination room and has an electronic medical record function and an image viewer function. The electronic medical record apparatus 20 generates electronic medical record information for each patient and each diagnosis, and stores the electronic medical record information in an electronic medical record Data Base (DB) 262 (see FIG. 2). The electronic medical record apparatus 20 also transmits patient information, date, and medical act information, which are included in the electronic medical record information, to the medical business accounting system 40.

Here, the electronic medical record information is composed of the patient information (patient ID, patient name, sex, age, etc.), date, free description information, and the medical act information. The free description information is freely recorded by a doctor when he finds it necessary, and includes, for example, findings, a main complaint, past illnesses, fondness, medical images (reduced images) used in diagnosis, and so on. The medical act information indicates a medical act that a doctor has performed to a patient, and includes, for example, an injury and disease name, medication (prescription), procedure, injection, examination/test, operation/surgery, image diagnosis, rehabilitation, and so on.

The reception apparatus 30 is a computer apparatus which is disposed at a reception desk and receives inputs of reception information (reception date, receipt number, and patient information of patient who has enrolled at the reception desk) of each patient. The reception apparatus 30 stores the reception information which has been input, and transmits the reception information to the electronic medical record apparatus 20 and the medical business accounting system 40.

The medical business accounting system 40 is a computer apparatus which performs accounting calculation, calculation of insurance points, and so on. The medical business accounting system 40 receives the patient information, date, and medical act information, which are included in the electronic medical record information, from the electronic medical record apparatus 20. The medical business accounting system 40 converts medical acts included in the medical act information into medical remuneration points, performs accounting calculation and/or calculation of insurance points, and generates receipt data. The receipt data is information of certificates (receipt) of medical remuneration for requesting, with regard to a medical care to the patient, payment of medical expenses to an insurer (municipality, health insurance union, etc.) from a medical institution. In the receipt data, there are written the patient information (patient name, sex, birth date, etc.), health insurance participation information of a patient, a name of medical institution as a biller, a medical department, medical act information, medical remuneration points corresponding to each medical act included in the medical act information.

Incidentally, the number of apparatuses/systems constituting the diagnosis system 1 is not particularly limited.

As a communication system in the diagnosis system 1, Digital Imaging and Communications in Medicine (DICOM) standard is generally used, and in communication among the respective apparatuses/systems, DICOM Modality Worklist Management (MWM) and/or DICOM Modality Performed Procedure Step (MPPS) are used.

[Configuration of Electronic Medical Record Apparatus]

FIG. 2 illustrates a functional configuration of the electronic medical record apparatus 20.

As illustrated in FIG. 2, the electronic medical record apparatus 20 is configured to include a control section 21, an operation section 22, a display section 23, a communication section 24, a Random Access Memory (RAM) 25, a storage section 26, and so on. The respective sections are connected to one another by a bus 27.

The control section 21 is composed of a Central Processing Unit (CPU) and others, and totally controls processing operations of respective sections of the electronic medical record apparatus 20. Concretely, the CPU reads out various programs stored in the storage section 26 to expand the programs in the RAM 25, in accordance with operation signals input from the operation section 22 or instruction signals received by the communication section 24, and performs various processes in cooperation with the programs. The control section 21 functions as a control member in cooperation with an electronic medical record function program P1 and an image viewer function program P2.

The operation section 22 is composed of a keyboard which includes cursor keys, numeral input keys, various function keys, etc., and a pointing device such as a mouse, etc., and outputs to the CPU 21 operation signals input by key pressing operation with respect to a keyboard and/or by mouse operation.

The operation section 22 may has a configuration which includes a touch panel including transparent electrodes arranged in a reticular pattern so as to cover a surface of the display section 23, detects positions pressed by a finger, touch pen, etc., and transmits obtained positional information, as operational information, to the control section 21.

The display section 23 is configured to include a monitor such as an Liquid Crystal Display (LCD), and displays various screens according to instructions of display signals input from the control section 21.

The communication section 24 is composed of a network interface and the like, and performs data transmission/reception with an external device connected to the electronic medical record apparatus 20 via the communication network N. For example, the communication section 24 receives the reception information from the reception apparatus 30. The communication section 24 also receives the medical images which have been obtained by photographing a patient by using the modality 10. Moreover, the communication section 24 transmits the patient information, date, and medical act information, which are of the electronic medical record information, to the medical business accounting system 40.

The RAM 25 forms a work area for temporarily storing various programs read out from the storage section 26, input/output data, parameters, etc., in each of various processes executed/controlled by the control section 21.

The storage section 26 is composed of a Hard Disk Drive (HDD), a non-volatile memory, or the like, and stores various programs, and data necessary for executing these programs.

Concretely, the storage section 26 stores the electronic medical record function program P1, the image viewer function program P2, a reception list DB 261, an electronic medical record DB 262, an image DB 263, a setting information file 264, and so on.

The electronic medical record function program P1 is a program for exerting functions (electronic medical record function) of generating, displaying, transferring, and/or storing the electronic medical record information, etc.

The image viewer function program P2 is a program for exerting functions (image viewer function) of storing and displaying the medical images, etc.

Incidentally, though this embodiment has the configuration where the electronic medical record function program P1 and the image viewer function program P2 are stored in the storage section 26, these programs may be Software as a Service (SaaS) type that is downloaded by accessing an external data management server via an internet or the like when the electronic medical record apparatus 20 is activated.

The reception list DB 261 is a database for storing reception information which has been transmitted from the reception apparatus 30 by the communication section 24 and has been received by the communication section 24.

The electronic medical record DB 262 is a database for storing the generated electronic medical record information.

The image DB 263 is a database for storing the medical images which have been transmitted from the modality 10 by the communication section 24, and have been received by the communication section 24, so that each medical image is correlated with each piece of the patient information.

Figure 4A:
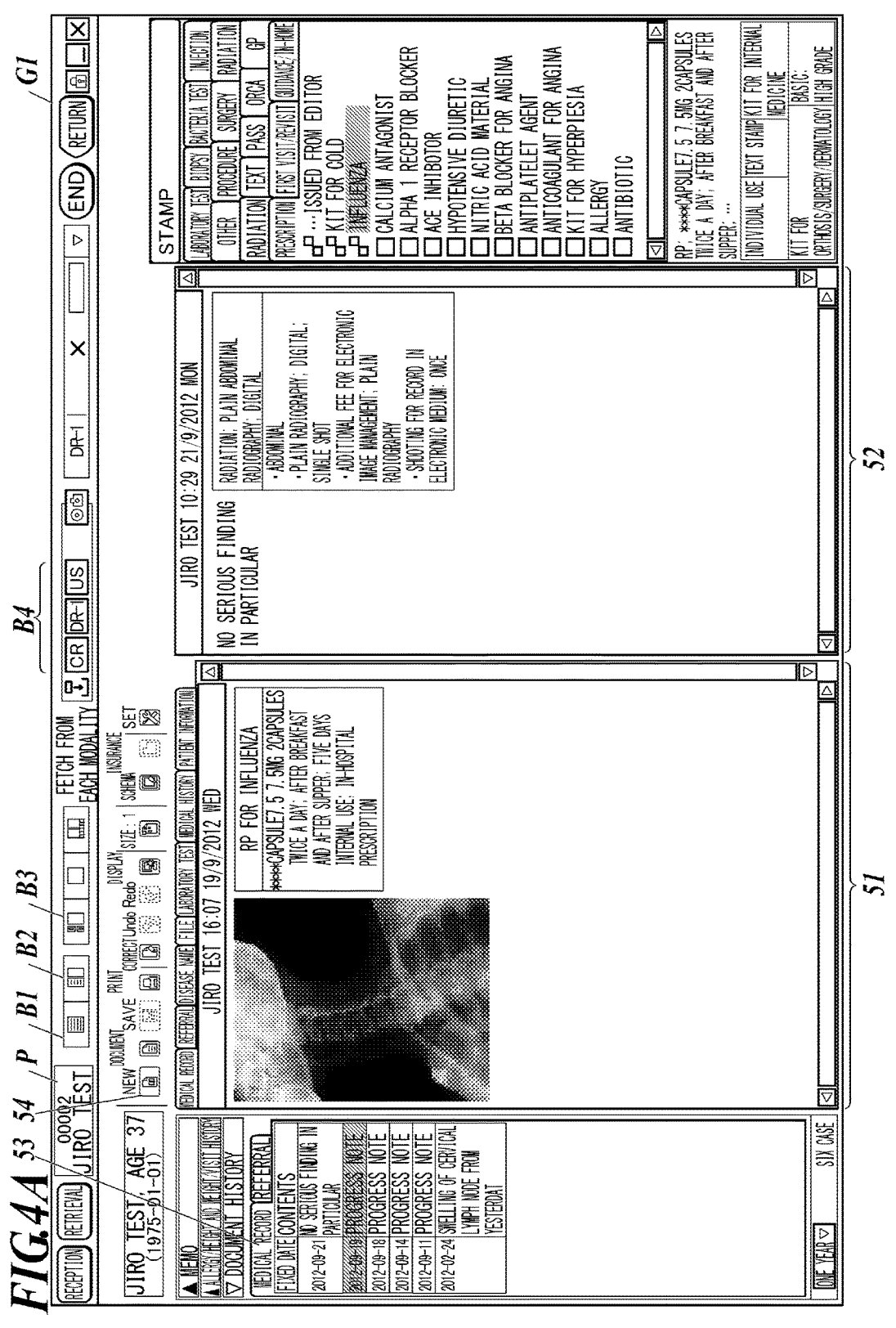

The setting information file 264 is a file which stores various pieces of setting information relevant to the electronic medical record apparatus 20. The setting information includes, for example: setting information (hereinafter referred to as setting information of "with automatic painting" or "without automatic painting") indicating whether or not the reduced image of the fetched medical image is automatically pasted on an after-mentioned new medical record input region 52a (see FIG. 4B) when the medical image taken in the modality 10 is fetched during display of the new medical record input region 52a; and setting information (hereinafter referred to as setting information of "with automatic switching", "without automatic switching", or "with report") indicating which of processes is performed. The processes are: automatically switching a current screen to a medical record viewer screen G2 (see FIG. 5); not switching the screen (with no report); and reporting that a new medical image has been fetched without switching the screen. These pieces of setting information can be set by a user (doctor) from a not-illustrated setting screen by operations in the operation section 22 (setting member). Incidentally, fetching the medical images taken in the modality 10 means receiving the medical images, which have been taken in the modality 10 and transmitted therefrom, by the electronic medial chart apparatus 20, and storing the medical images in the image DB 263 so that each medical image is correlated with each piece of the patient information.

[Operation of Diagnosis System 1]

Next, a flow of diagnosis and an operation of the diagnosis system 1 in the case that one (1) patient visits a small-scale medial facility, such as an office of a practitioner and a clinic, will be described.

When the patient comes to the medical facility, firstly, an operator operates the reception apparatus 30 disposed at the reception desk to perform an input (reception input) of the patient information. When the patient information has been input, the reception apparatus 30 issues the receipt number, and generates the reception information including the receipt number, reception date, and patient information. Then, the generated reception information is stored in the storage section thereof, and is transmitted to the electronic medical record apparatus 20 and the medical business accounting system 40 via the communication network N.

When the patient with the given receipt number has transferred to the examination room, the doctor starts a medical interview there. In the medical interview, the doctor opens/displays a medical record screen G1 of the patient concerned by specifying the patient who is a diagnosis object in the operation section 22 of the electronic medical record apparatus 20, and refers to a past medical record to confirm a medical history of the patient. The doctor then determines what kind of photographing, examination, and/or treatment should be performed, on the basis of the medical interview and/or the medical history. In the case that photographing should be performed, the patient is led to transfer to the photographing room and photographing is performed by using the modality and the like.

After photographing, the doctor refers to the medical images obtained by the photographing to perform diagnosis. The doctor then inputs medical acts which have been performed, and diagnosis outcome, on the medical record screen G1 of the patient concerned. The electronic medical record apparatus 20 creates the electronic medical record information on the basis of the information input on the medical record screen G1, stores the electronic medical record information in the electronic medical record DB 262, and transmits the patient information, date, and medical act information to the medical business accounting system 40. The medical business accounting system 40 then performs calculation of insurance points, etc.

Heretofore, the electronic medical record apparatus has issued photographing order information, but even when issuing the photographing order information in the electronic medical record apparatus, additional operations such as displaying a list of pieces of the photographing order information in a console of the modality in the photographing room, selecting the photographing order information of a photographing object, and confirming an image display have been necessary. Such operations are very troublesome for being managed by one (1) doctor, and reduce the efficiency. Moreover, because the medical images are fed into the medical image management apparatus (for example, see Japanese Patent Application Laid-open No. 2010-124943) to be stored therein and managed thereby, in the case that the doctor wants to paste the medical images obtained by photographing in the electronic medical record information, additional operations of obtaining the medical images from the modality and/or the medical image management apparatus and pasting the obtained medical images in the information become necessary, which operations are troublesome.

To solve these problems, the electronic medical record apparatus 20 is equipped with the electronic medical record function program P1 and the image viewer function program P2, and enables: automatically correlating each medical image, which has been taken by the modality and transmitted therefrom, with each piece of patient information of the patient whose medical record screen G1 is currently being displayed, to store them in the image DB 263; displaying the medical image on the medical record screen G1; and pasting the medical image, as the reduced image, in new electronic medical record information of the patient concerned, by cooperation between the electronic medical record function program P1 and the image viewer function program P2. In other words, correlating the medical image with the patient information, which has been impossible by the conventional electronic medical record screen, can be easily performed by a simple operation in the flow of diagnosis. Also pasting the medical image in the electronic medical record information can be performed by a simple operation.

Hereinafter, a flow of image fetch/display processing when in the flow of diagnosis the electronic medical record apparatus 20 fetches the medical images from the modality 10 to display them will be described.

FIG. 3 illustrates the flow of the image fetch/display processing which is executed by the electronic medical record apparatus 20 and the modality 10. The processes to be executed in the electronic medical record apparatus 20 are performed by the control section 21 in cooperation with the electronic medical record function program P1 and the image viewer function program P2. The processes to be executed in the modality 10 as illustrated in FIG. 3 are performed by a control section (not illustrated) of the modality 10 in cooperation with a control program therefor.

FIG. 3 illustrates an operation example in the case that the pieces of setting information of "with automatic painting" and "with automatic switching" are set in the setting information file 264.

When a doctor inputs instruction to display a reception list screen (not illustrated) by an operation in the operation section 22 of the electronic medical record apparatus 20, the control section 21 reads out the reception information whose reception date is today from the reception list DB 261 stored in the storage section 26, and causes the display section 23 to display the reception list screen, in accordance with the electronic medical record function program P1 (Step S1). The reception list screen is a screen in which a list of pieces of the patient information of patients who has enrolled at the reception desk is displayed, and the patient to be examined can be specified from this reception list screen by using the operation section 22 (patient specifying member).

When the patient information of the patient to be examined is specified from the reception list screen displayed on the display section 23 by using the operation section 22 of the electronic medical record apparatus 20 (Step S2), the control section 21 causes the display section 23 to display the medical record screen G1 relevant to the specified patient in accordance with the electronic medical record function program P1 (Step S3).

FIG. 4A illustrates an example of the medical record screen G1. As illustrated in FIG. 4A, the medical record screen G1 includes a patient information display region P, display mode selection buttons B1-B3, image fetch buttons B4, a medical record display region 51, a medical record display region 52, a past medical record selection region 53, a new medical record button 54, and so on.

The patient information display region P is a region for displaying the patient information which has been specified in Step S2.

The display mode selection buttons B1-B3 are buttons for selecting a screen display mode in the display section 23. The display mode selection button B1 is a button for selecting, as the screen display mode, a medical record display mode in which the medical record screen G1 is displayed over the entire area of the screen in the display section 23.

The display mode selection button B2 is a button for selecting, as the screen display mode in the display section 23, a medical record viewer display mode in which the medical record viewer screen G2 is displayed in the display section 23. FIG. 5 illustrates an example of the medical record viewer screen G2. The medical record viewer screen G2 includes a region 61 for displaying the medical record screen G1 and a region 62 for displaying a viewer screen G3, and displays both of the screens simultaneously. A current screen can be switched to the medical record viewer screen G2 by pressing the display mode selection button B2 by using the operation section 22 to select the medical record viewer display mode.

The display mode selection button B3 is a button for selecting, as the screen display mode in the display section 23, a viewer display mode in which the viewer screen G3 is displayed on the entire area of the screen in the display section 23. FIG. 6 illustrates an example of the viewer screen G3. The viewer screen G3 includes a medical image display region 71 for displaying the medical images of the patient to be examined. The doctor examines the medical images on the viewer screen G3 to perform radiologic interpretation and diagnosis. The viewer screen G3 can be displayed by pressing the display mode selection button B3 by using the operation section 22 to select the viewer display mode.

Each of the image fetch buttons B4 is a fetch instruction member for receiving an instruction to fetch the medical images transmitted from the modality 10, as the medical images of the patient (the medical record screen G1 therefor is being displayed) specified as a diagnosis object. The image fetch buttons B4 are provided for respective kinds of the modalities 10, such as "CR", "DR-1 (FPD)", and "US".

The medical record display regions 51, 52 are regions for displaying a past medical record (past electronic medical record information) selected from the past medical record selection region 53, or the new medical record input region 52a for receiving an input of new electronic medical record information. Incidentally, by default, as illustrated in FIG. 4A, two pieces of past electronic medical record information, which have been created most recently, are displayed in the medical record display regions 51, 52, respectively.

The new medical record button 54 is a button for instructing to display the new medical record input region 52a, namely, to open a new medical record, in the medical record display region 52.

When the new medical record button 54 is pressed by the operation section 22 in the electronic medical record apparatus 20, the control section 21 opens the new medical record, namely, displays the new medical record input region 52a in the medical record display region 52 of the medical record screen G1 displayed in the display section 23 (Step S4).

Figure 4B:
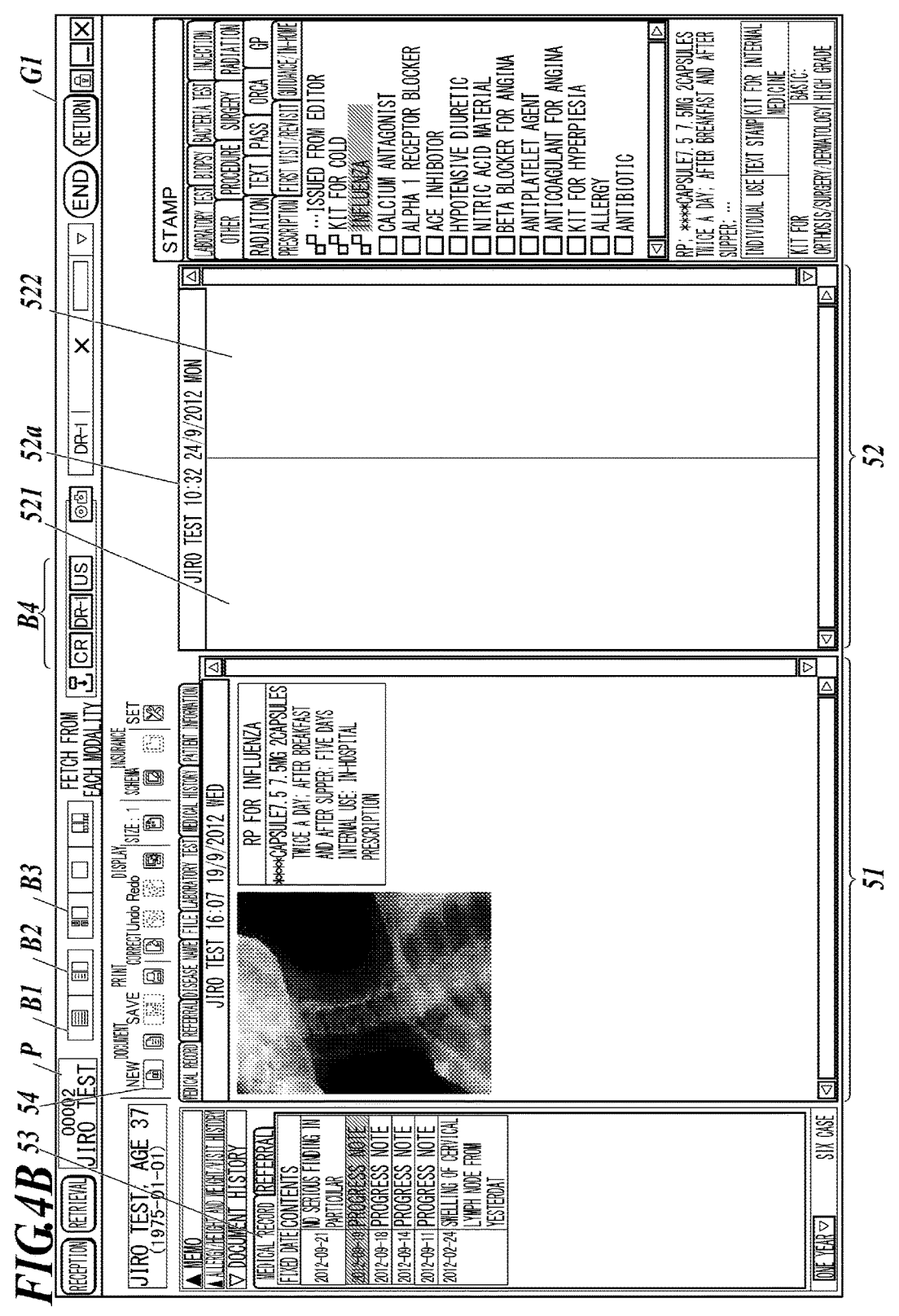

FIG. 4B illustrates an example of the medical record screen G1 in which the new medical record input region 52a is displayed. The new medical record input region 52a includes a free description region 521 and a medical act region 522. The free description region 521 is a region in which the above-described free description information is input. The medical act region 522 is a region in which the above-described medical act information is input.

When one of the image fetch button B4 is pressed by the operation section 22 in the electronic medical record apparatus 20 (Step S5), the control section 21 outputs image fetch instruction information to the image viewer function program P2 in accordance with the electronic medical record function program P1 (Step S6). The image fetch instruction information is a file which indicates information indicating a kind ("CR", here) of the modality 10 corresponding to the pressed image fetch button B4, a patient ID of the currently-displayed medical record screen G1, and the fact that the image fetch button B4 of the CR is turned ON, for example, like "Modality: CR, Patient ID: 001, CR Online: ON".

Next, the control section 21 interprets the image fetch instruction information according to the image viewer function program P2 (Step S7), and transmits an instruction to be on standby for photographing by the communication section 24, with respect to the modality 10 of the kind corresponding to the pressed image fetch button B4 (Step S8). The control section 21 is also set to a standby state for receiving the medical images from the modality 10 (Step S9).

When receiving the instruction from the electronic medical record apparatus 20, the modality 10 is set to a standby state for photographing. The modality 10 then performs photographing of the diagnosis target region of the patient according to the operations by the doctor and/or photography technician (Step S11), and transmits the medical images obtained by photographing to the electronic medical record apparatus 20 via the communication network N (Step S12).

When the electronic medical record apparatus 20 has received the medical images by the communication section 24 from the modality 10 (Step S13), the control section 21 correlates each received medical image with each piece of patient information of the currently-displayed medical record screen G1, and stores them in the image DB 263, in accordance with the image viewer function program P2 (Step S14).

After that, the control section 21 creates the reduced images by reducing the medical images in accordance with the image viewer function program P2 (Step S15). The reduced images are images of JPEG format or the like, for example. The control section 21 then outputs the created reduced images, image information, medical record layout instruction information to the electronic medical record function program P1 in accordance with the image viewer function program P2 (Step S16). The image information is a file which indicates a kind ("CR", here) of the modality 10 which has been used in photographing, a patient ID, a photographing portion ("chest", here), for example, like "Modality: CR, Patient ID: 001, Body Part: Chest". The medical record layout instruction information is information for instructing to automatically switch a current screen to the medical record viewer screen G2, for example, like "Layout: mix".

Next, the control section 21 changes the display layout on the screen of the display section 23, and performing automatic display switching to the medical record viewer screen G2 in the display section 23, in accordance with the electronic medical record function program P1 (Step S17). The control section 21 then automatically pastes and displays the reduced image of the medical image, which has been obtained by photographing, in the new medical record input region 52a of the medical record screen G1 displayed in the region 61, in accordance with the electronic medical record function program P1 (Step S18). The control section 21 also displays the medical image, which has been received from the modality 10, in the medical image display region 71 of the viewer screen G3 displayed in the region 62, in accordance with the image viewer function program P2 (Step S19).

FIG. 5 illustrates an example of the medical record viewer screen G2 to be displayed in the display section 23 after processes of Steps S18 and S19.

According to the image fetch/display processing, in the electronic medical record apparatus 20, the patient to be examined is specified and then the medical record screen G1 is displayed, and when pressing one of the image fetch buttons B4 on the medical record screen G1 by using the operation section 22, the medical image taken by the modality 10 of the kind corresponding to the pressed image fetch button B4 is automatically fed into the electronic medical record apparatus 10. Then, as illustrated in FIG. 5, the screen layout in the display section 23 is automatically switched to the medical record viewer screen G2, the viewer screen G3 of the fed medical image is displayed in the region 62, and at the same time, the reduced image of the medical image is automatically pasted in the new medical record input region 52a of the medical record screen G1 displayed in the region 61.

Therefore, the doctor can correlate the medical image taken by the modality 10 with the patient information by a simple operation of pressing the image fetch button B4 on the medical record screen G1 of the patient as a diagnosis object (i.e. a photographing object), which screen is displayed in the flow of diagnosis, without performing troublesome operations, which have been conventionally performed, such as displaying the list of pieces of photographing order information in the console of the modality 10, selecting the photographing order information of the photographing object, and confirming the image display. This can improve operability at the time of diagnosis, and diagnosis efficiency. Moreover, because the operation of causing the display section 23 to display the medical images so that the medical images can be referred to, and/or the operation of fetching the reduced images of the taken medical images from the modality 10 and/or the medical image management apparatus to paste the reduced images in the new electronic medical record information become unnecessary, the operability and the diagnosis efficiency are further improved.

Incidentally, in the case that a plurality of modalities 10 perform photographing, after one of the image fetch buttons B4 corresponding to the respective modalities 10 is pressed, pressing operations of the other image fetch buttons B4 are invalidated until the process of Step S19 is terminated. When the image fetch button B4 of another modality 10 is pressed after Step S19 is terminated, the control section 21 performs the process of Step S6 and subsequent processes thereof to correlate the medical images, which have been taken by the another modality 10 and transmitted therefrom, with the patient information of the patient, the medical record screen G1 being displayed currently for the patient, to store them, and to paste the reduced images of the medical images in the new medical record input region 52*a*.

When the diagnosis is terminated and the medical record screen G1, which has been being displayed, is closed, the control section 21 creates the electronic medical record information based on the information input from the new medical record input region 52*a*, stores the electronic medical record information in the electronic medical record DB 262, and transmits the patient information, date, and medical act information to the medical business accounting system 40, according to the electronic medical record function program P1.

[Variation]

Next, a variation of the above embodiment will be described.

Although the electronic medical record function program P1 and the image viewer function program P2 are independent from each other in the description of the above embodiment, the electronic medical record function program P1 can also be activated to operate on the image viewer function program P2.

In addition, the image fetch buttons B4 can exist on the image viewer function program P2.

FIG. 7 illustrates a flow of the image fetch/display processing in the case that the image fetch buttons B4 exist on the image viewer function program P2 and the electronic medical record function program P1 is activated to operate on the image viewer function program P2. The processes to be executed in the electronic medical record apparatus 20 illustrated in FIG. 7 are performed by the control section 21 in cooperation with the electronic medical record function program P1 and the image viewer function program P2. The processes to be executed in the modality 10 illustrated in FIG. 7 are performed by the control section (not illustrated) of the modality 10 in cooperation with the control program therefor.

Incidentally, FIG. 7 illustrates an operation example in the case that the pieces of setting information of "with automatic pasting" and "with automatic switching" are set. The respective screens to be displayed are similarly to those of the above embodiment.

When the electronic medical record apparatus 20 receives from a doctor the instruction to display the reception list screen, input by operation in the operation section 22, the control section 21 reads out the reception information whose reception date is today from the reception list DB 261 stored in the storage section 26 to cause the display section 23 to display the reception list screen, according to the image viewer function program P2 (Step S31).

When the information of the patient to be examined is specified from the reception list screen displayed in the display section 23 by using the operation section 22 (Step S32), the control section 21 causes the display section 23 to display the viewer screen G3 relevant to the specified patient who is a diagnosis object, according to the image viewer function program P2 (Step S33). When the display mode selection button B1 is pressed from the viewer screen G3 by using the operation section 22, the control section 21 activates the electronic medical record function program P1 and outputs the patient ID of the patient as the diagnosis object to the electronic medical record function program P1, according to the image viewer function program P2 (Step S34).

When the electronic medical record function program P1 is activated, the control section 21 causes the display section 23 to display the medical record screen G1 of the patient whose patient ID has been output by the image viewer function program P2, according to the electronic medical record function program P1 (Step S35).

When one of the image fetch buttons B4 displayed on the screen of the display section 23 is pressed by using the operation section 22 (Step S36), the control section 21 transmits the instruction to be on standby for photographing to the modality 10 of the kind corresponding to the pressed image fetch button B4 by the communication section 24 (Step S37). The control section 21 is also set to a standby state for receiving the medical images from the modality 10 (Step S38).

Because the process of Step S39 and subsequent processes thereof are similar to the process of Step S10 and subsequent processes thereof, the explanation of the latter is employed by the former.

Thus, also in the configuration where the electronic medical record function program P1 is activated to operate on the image viewer function program P2, by pressing the image fetch button B4, the medical images which have been taken by the modality 10 can be fed into the electronic medical record apparatus 20, as the medical images of the patient of the currently-opened medical record screen G1. Also automatic display switching to the medical record viewer screen G2 and pasting of the reduced images of the medical images on the new medical record are possible.

Also in this variation, as is the case with the above embodiment, after image fetch from one (1) modality 10 is terminated (after the process of Step S48 is terminated), by executing the process of Step S37 and subsequent processes depending on the image fetch button B4 pressed and corresponding to another modality 10, the medical images taken by a plurality of kinds of modalities 10 can be sequentially correlated to the pieces of patient information of the patient of the currently-displayed medical record screen G1, respectively, so that they are stored in such a state, and the reduced images of the medical images can be pasted in the new medical record input region 52*a*.

When the diagnosis is terminated and the medical record viewer screen G2 (or medical record screen G1), which has been being displayed, is closed by operation in the operation section 22, the control section 21 creates the electronic medical record information on the basis of the information input from the new medical record input region 52*a*, stores it in the electronic medical record DB 262, and transmits it to the medical business accounting system 40, according to the electronic medical record function program P1.

Although the above embodiment and variation describe the case that the pieces of setting information of "with automatic pasting" and "with automatic switching" are set in the setting information file 264, in the case that the setting information of "without automatic pasting" is set, the control section 21 omits the process of Step S18 in FIG. 3, or process of Step S47 in FIG. 7. In the case that "without automatic switching" is set, the control section 21 omits outputting the medical record layout instruction information of Step S16 in FIG. 3 or Step S45 in FIG. 7, the process of Step S17 in FIG. 3 or Step S46 in FIG. 7, and the process of Step S19 in FIG. 3 or Step S48 in FIG. 7. In the case that "with report" is set, the control section 21 outputs image fetch report information instead of outputting the medical record layout instruction information of Step S16 in FIG. 3 or Step S45 in FIG. 7, and displays an image fetch report on the medical record screen G1 without changing the display layout in Step S17 in FIG. 3 or Step S46 in FIG. 7. As an example of the image fetch report, for example, a message such as "Image fetch is completed" can be displayed on a pop-up, and/or an indicator which indicates the image fetch report can be displayed. It is also possible to omit the process of Step S17 or Step S46 in FIG. 7, and to display the reduced image on the new medical record as the image fetch report.

As described above, according to the electronic medical record apparatus 20, when the image fetch button B4 is pressed on the medical record screen G1 by using the operation section 22, the control section 21 correlates the medical image transmitted from the modality 10 with the patient information of the patient whose medical record screen G1 is currently displayed in the display section 23, and stores them in the image DB 263.

Therefore, the doctor can correlate the medical image taken by the modality 10 with the patient information by a simple operation of pressing the image fetch button B4 on the medical record screen G1 of the patient as the diagnosis object (i.e. photographing object), which screen is displayed in the flow of the diagnosis, without performing troublesome operations including displaying the list of pieces of photographing order information in the console of the modality, selecting the photographing order information of the photographing object, and confirming the displayed image. This can drastically improve the operability and the diagnosis efficiency.

When the image fetch button B4 is pressed on the medical record screen G1, the control section 21 automatically pastes the medical images transmitted from the modality 10 in the new medical record input region 52*a* of the medical record screen G1. Thus, the operation of causing the display section 23 to display the medical images so that the same can be referred to at the time of creating the electronic medical record, and/or the operation of fetching the reduced images of the taken medical images from the modality 10 and/or the medical image management apparatus to paste the reduced images in the new electronic medical record information become unnecessary, and thereby operability and diagnosis efficiency can be further improved.

It is preferable to paste the reduced image obtained by reducing the medical image in the new medical record input region 52*a*. By this, the medical image can be pasted in the new medical record input region 52 without interrupting input of the other electronic medical record information.

Moreover, it is preferable that whether or not the medical image transmitted from the modality 10 is pasted in the new medical record input region 52*a* can be set in the operation section 22. By this, in the case that a doctor, namely a user, thinks necessary, the medical image taken by the modality 10 can be automatically pasted in the new medical record input region 52*a*.

Incidentally, the description of the above embodiment is mere example of the electronic medical record apparatus according to the present invention, and the present invention is not limited thereto.

For example, though in the above embodiment and variation, by default, two pieces of past electronic medical record information which have been created most recently are displayed in the medical record display regions 51, 52 of the medical record screen G1 as illustrated in FIG. 4A, it is also possible to display the new medical record input region 52*a* in the medical record display region 51 or 52.

Moreover, though the above embodiment and variation describe as an example the case that the image fetch button B4 is pressed while the new medical record input region 52*a* is being displayed in the medical record display region 52, also in the case that the image fetch button B4 is pressed while the past electronic medical record information is displayed in the medical record display region 52, the processes similar to those illustrated in FIG. 3 or FIG. 7 are performed. In this regard, however, because the new medical record input region 52*a* is not displayed in Step S18 in FIG. 3 or Step S47 in FIG. 7, the control section 21 makes the RAM 25 store the reduced image according to the electronic medical record function program P1. Then, when the new medical record button 54 is pressed by using the operation section 22 and the new medical record input region 52*a* is displayed, the control section 21 pastes the reduced image stored in the RAM 25 in the new medical record input region 52*a* to display the reduced image according to the electronic medical record function program P1.

Furthermore, though the electronic medical record apparatus 20 of the above embodiment has two programs of the electronic medical record function program P1 and the image viewer function program P2 so that the control section 21 exerts the functions of executing the processes of the image fetch/display processing to be performed in the electronic medical record apparatus 20 in cooperation with these two programs, the functions of these two programs may be integrated into one (1) program.

Additionally, though the above descriptions disclose the example where the Hard Disk Drive (HDD) and/or non-volatile memory are used as a computer readable medium which stores the programs for executing the respective processes, the present invention is not limited to the example. As another computer readable medium, a portable recording medium such as CD-ROM can be adopted. In addition, as a medium for providing data of the programs via a communication line, a carrier wave can be adopted.

Other detailed configurations and detailed operations of the electronic medical record apparatus can be arbitrarily changed without departing from the spirit of the present invention.

The present U.S. patent application claims a priority under the Paris Convention of Japanese patent application No. 2012-273426 filed on Dec. 14, 2012, in which all contents of this application are disclosed, and which shall be a basis of correction of an incorrect translation.

What is claimed is:

1. An electronic medical record apparatus connected to a plurality of kinds of image generation apparatuses which perform photographing of a diagnosis target region of a patient to generate a medical image, the electronic medical record apparatus comprising:

a storage;

an input device to receive an input of specifying a patient to be examined;

a display to display a medical record screen in which electronic medical record information pertaining to the patient specified by the input device is displayed;

a plurality of fetch instruction operators provided respectively for each of the kinds of the image generation apparatuses, on the medical record screen displayed on the display, and which are operable to receive, before photographing is performed, a fetch instruction to fetch a medical image of the patient corresponding to the medical record screen;

a communication device to communicate with the plurality of kinds of image generation apparatuses; and a CPU which is configured to:

generate, in response to operation of one of the fetch instruction operators, image fetch instruction information including (i) at least a part of patient information of the patient corresponding to the medical record screen displayed at a time of operation of said one of the fetch instruction operators and (ii) information specifying the image generation apparatus of the kind corresponding to the operated fetch instruction operator;

control, based on the generated image fetch instruction information and in response to operation of said one of the fetch instruction operators, the communication device to transmit a standby instruction to the specified image generation apparatus which is specified in the image fetch instruction information, the standby instruction instructing the specified image generation apparatus to be on standby for photographing, and control, in response to operation of said one of the fetch instruction operators, the electronic medical record apparatus to be set to a standby state for receiving medical images from the specified image generation apparatus;

after having set the electronic medical record apparatus to be in the standby state and after the specified image generation apparatus to which the standby instruction was transmitted performs photographing and transmits the generated medical image to the electronic medical apparatus, receive, while in the standby state, via the communication device, the medical image transmitted from the specified image generation apparatus, wherein the specified image generation apparatus automatically transmits the generated medical image to the electronic medical record apparatus after photographing; and store, based on the image fetch instruction information, the medical image received from the specified image generation apparatus in the storage so that the medical image is automatically correlated with the patient information of the patient specified in the image fetch instruction information.

2. The electronic medical record apparatus of claim 1, wherein:

the medical record screen includes a new medical record input region in which new electronic medical record information is input, and the CPU further performs control to paste the medical image, which has been transmitted from the image generation apparatus of the kind corresponding to the operated fetch instruction operator, in the new medical record input region on the medical record screen displayed on the display device, when the communication device receives the medical image which is transmitted from the image generation apparatus of the kind corresponding to the operated fetch instruction operator.

3. The electronic medical record apparatus of claim 2, wherein the input device is further configured to receive an input of a setting as to whether or not to paste the medical image transmitted from the image generation apparatus of the kind corresponding to the operated fetch instruction operator in the new medical record input region.

4. The electronic medical record apparatus of claim 2, wherein the medical image to be pasted in the new medical record input region is a reduced image obtained by reducing the medical image.

5. A non-transitory computer readable recording medium having recorded thereon a program for controlling a CPU of an electronic medical record apparatus, the electronic medical apparatus being connected to a plurality of kinds of image generation apparatuses so that data transmission/reception can be performed between the apparatuses, the image generation apparatuses performing photographing of a diagnosis target region of a patient to generate a medical image, and the program being executable to control the CPU to perform functions comprising:

receiving an input of specifying patient information of a patient to be examined;

displaying, on a display, a medical record screen in which electronic medical record information pertaining to the patient specified by the receiving is displayed;

displaying, on the medical record screen displayed on the display, a plurality of fetch instruction operators provided respectively for each of the kinds of the image generation apparatuses, and which are operable to receive, before photographing is performed, a fetch instruction to fetch a medical image of the patient corresponding to the medical record screen;

generating, in response to operation of one of the fetch instruction operators, image fetch instruction information including (i) at least a part of patient information of the patient corresponding to the medical record screen displayed at a time of operation of said one of the fetch instruction operators and (ii) information specifying the image generation apparatus of the kind corresponding to the operated fetch instruction operator;

transmitting, based on the generated image fetch instruction information and in response to operation of said one of the fetch instruction operators, a standby instruction to the specified image generation apparatus which is specified in the image fetch instruction information, the standby instruction instructing the specified image generation apparatus to be on standby for photographing, and controlling, in response to operation of said one of the fetch instruction operators, the electronic medical record apparatus to be set to a standby state for receiving medical images from the specified image generation apparatus;

after having set the electronic medical record apparatus to be in the standby state and after the specified image generation apparatus to which the standby instruction was transmitted performs photographing and transmits the generated medical image to the electronic medical apparatus, receiving, while in the standby state, the medical image transmitted from the specified image generation apparatus, wherein the specified image generation apparatus automatically transmits the generated medical image to the electronic medical record apparatus after photographing;

storing, based on the image fetch instruction information, the medical image received from the specified image generation apparatus in a storage so that the medical image is automatically correlated with the patient information of the patient specified in the image fetch instruction information.

* * * * *